United States Patent [19]

Steffen

[11] Patent Number: 5,510,509
[45] Date of Patent: Apr. 23, 1996

[54] PREPARATION OF ESTERS OF CYCLOPROPANE-1,1-DICARBOXYLIC ACID

[75] Inventor: Klaus-Dieter Steffen, Hennef, Germany

[73] Assignee: Hüls Aktiengesellschaft, Marl, Germany

[21] Appl. No.: 287,156

[22] Filed: Aug. 8, 1994

[30] Foreign Application Priority Data

Aug. 11, 1993 [DE] Germany ............. 43 26 917.6

[51] Int. Cl.$^6$ .................................. C07C 69/74
[52] U.S. Cl. ............................................. 560/124
[58] Field of Search ............................... 560/124

[56] References Cited

PUBLICATIONS

Chem. Abstr. 122:31000 (1993).
Chem. Abstr. 108:74841 (1987).
Chem. Abstr. 119:116838 (1993).
Chem. Abstr. 110:153771 (1988).

*Primary Examiner*—Michael L. Shippen
*Attorney, Agent, or Firm*—Felfe & Lynch

[57] ABSTRACT

Dialkyl cyclopropane-1,1-dicarboxylates are prepared from a dialkyl malonate, a 1,2-dichloroalkane and finely divided potassium carbonate while azeotropically removing the water released by the reaction.

1 Claim, No Drawings

PREPARATION OF ESTERS OF CYCLOPROPANE-1,1-DICARBOXYLIC ACID

FIELD OF THE INVENTION

This invention relates to a novel process for the preparation of esters of cyclopropane-1,1-dicarboxylic acid from a dialkyl malonate, a 1,2-dihalo alkane and potassium carbonate in dimethylformamide or dimethylacetamide.

BACKGROUND OF THE INVENTION

The cycloalkylation of dimethyl malonate with 1,2-dibromoethane in potassium carbonate/dimethylformamide is disclosed by D. A. White in Synthesis Communications 7/8 (1977) 559. Based on 1 mol of dimethyl malonate, 4 mols of dibromoethane and 2.4 mols of potassium carbonate in 1.2 liters of dimethylformamide are reacted for 22 hours, yielding 73% of theory of dimethyl cyclopropane-1,1-dicarboxylate (CDM). These are data of a poor space-time yield which stands in the way of using the method on an industrial scale. A further target must be to replace the 1,2-dibromoethane with 1,2-dichloroethane, for instance. However, dichlorides are not very reactive. The comparative example below shows that 1,2-dichoroethane produces CDM with a yield of 55% of theory, whereas 1,2-dibromoethane produces CDM with a yield of 96.5% of theory. The disposal of potassium chloride by electrolysis is simple, but the disposal of potassium bromide is not. Nonetheless, many attempts have been made to use the dichloride. Thus, J. Heiszman et al, Synthesis Communications 1987, 738, used benzene as a solvent medium and also used a phase transfer catalyst, which yielded diethyl cyclopropane-1,1-dicarboxylate (CDE) in over 20 hours at 80° C. The use of solvents such as benzene is no longer allowed. Phase transfer catalysts are difficult to dispose of and form amines during decomposition.

OBJECTS OF THE INVENTION

It is an object of the present invention to provide a method for preparing esters of cyclopropane-1,1-dicarboxylic acid (I) which avoids the shortcomings of the prior art methods.

Other objects of the present invention will become apparent as the description thereof proceeds.

DESCRIPTION OF THE INVENTION

I have discovered that the above mentioned objects are achieved by reacting a dialkyl malonate (II) with potassium carbonate and a 1,2-dichloroalkane (III) in dimethylformamide or dimethylacetamide pursuant to the following reaction sequence:

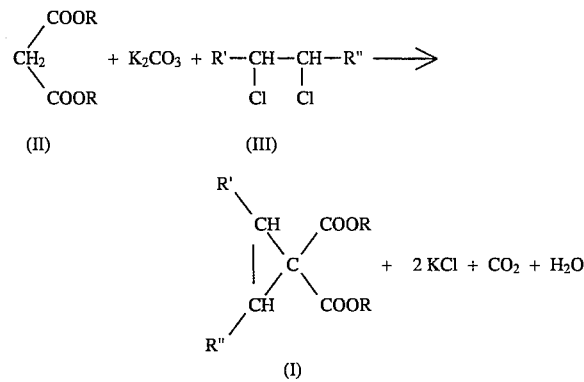

wherein

R is alkyl of 1 to 4 carbon atoms, and

R' and R", which may be identical to or different from each other are each hydrogen, methyl, ethyl or chlorine, provided that at least one of R' and R" is hydrogen, and further provided that a) the potassium carbonate is used in finely divided form wherein 85% or more of the particles are less than 0.1 mm mesh and 70% or more of the particles are less than 0.05 mm mesh, b) the water released by the reaction is azeotropically distilled off during the reaction, c) the reaction temperature is 90° to 160° C., and d) the molar ratio of dialkyl malonate: 1,2-dichloroalkane: potassium carbonate =1:(2.5 to 3.5) : (1.0 to 1.4).

Some of the end products of the formula I are novel, namely di-n-butyl cyclopropane-1,1-dicarboxylate, diisopropyl cyclopropane-1,1-dicarboxylate and 1,1-dicarbomethoxy-2-methylcyclopropane.

The cyclopropane-1,1-dicarboxylic acid esters embraced by formula I are useful as intermediates for the preparation of pharmaceuticals and insecticides.

To summarize, I have discovered that a) contrary to expectations, 1,2-dichloroalkanes can be advantageously used to prepare cyclopropane-1,1-dicarboxylic acid esters with yields of 80 to 85% of theory;

b) that potassium carbonate which is finely ground or in the form of dust has a significantly positive effect upon the conversion and yield of the target product. This fact is illustrated in the comparative example below. Using commercial potassium carbonate and 1,2-dibromoethane, D. A. White (loc.cit.) obtained 73% of theory of dimethyl cyclopropane-1,1-dicarboxylate, whereas when I used finely divided potassium carbonate the yield of dimethyl cyclopropane-1,1-dicarboxylate was 96% of theory.

c) To accelerate the conversion, the water formed by the reaction is distilled off azeotropically. The entrainment agent is preferably the 1,2-dichloroalkane itself. After condensation, an upper aqueous phase and a lower organic phase are formed, the latter being recycled into the reaction. Other entrainment agents may also be used, such as aliphatic hydrocarbons of up to 8 carbon atoms.

d) A further acceleration of the conversion is achieved by performing the reaction at a temperature of 90° to 160° C., preferably 110° to 130° C., whereby the reaction times for the formation of dimethyl cyclopropane-1,1-dicarboxylate and diethyl cyclopropane-1,1-dicarboxylate are reduced to 5 to 6 hours.

e) To improve the space-time yields, the amount of dimethyl-formamide or dimethylacetamide solvent is reduced. Preferably, only 200 to 300 ml of solvent are needed per mol of malonate. Phase transfer catalysts are then also superfluous. The required amounts of potassium carbonate and 1,2-dichloroalkane are reduced as well.

All of the reactants may be charged into the reaction vessel together and the mixture is then heated to the reaction temperature. The malonate, however, may also be metered in over the period of the reaction time.

The carbon dioxide waste gas is removed from the reaction by means of a condenser. Traces of vinyl chloride which may form can be frozen out in a cold trap. The removal of the salts, potassium chloride and potassium carbonate, can be effected in the two ways illustrated in the examples.

The flash distillates and filtrates from the workup are separated by distillation. The solvents and unreacted 1,2-dichloroalkanes can be used over again.

Since among the cyclopropane-1,1-dicarboxylic acid esters the methyl esters can be most readily prepared, the esters formed with alcohols having more than 3 carbon atoms can be prepared with high yields by transesterification of the methyl ester with the desired alcohol, using transesterification catalysts such as butyl titanate. However, the higher alkyl esters may also be prepared by the method of the present invention.

The following examples illustrate the present invention and will enable others skilled in the art to understand it more completely. It should be understood, however, that the invention is not limited solely to the particular examples given below.

The particle distribution in the comminuted potassium carbonate used in the examples was 88% smaller than 0.1 mm and 72% smaller than 0.05 mm.

Comparative Example Dimethyl cyclopropane-1,1-dicarboxylate by the method of D. A. White, loc. cit.

a) A glass reaction vessel equipped with a stirrer was charged successively with 500 ml of dimethylformamide, 66 g of dimethyl malonate (0.5 mol), 376 g of 1,2-dibromoethane (0.2 mol) and 166 g of finely comminuted potassium carbonate (1.2 mols). The mixture was stirred for 22 hours at room temperature, and subsequently for 2 hours at 100° C. The mixture of potassium chloride and potassium carbonate which separated out was filtered off, washed with dimethylformamide and dried, giving 234 g of salt. The distillate obtained from drying the salt was added to the filtrate. The crude reaction mixture was then distilled in vacuo over a column. After taking off dibromoethane and dimethyl-formamide, dimethyl cyclopropane-1,1-dicarboxylate distilled over at 85° C./18 mbar as a clear colorless liquid.

Yield: 77.0 g (96.5% of theory)
Purity: 99%

When potassium carbonate with a commercial particle size distribution was used, significantly lower yields of target product were obtained.

b) When 1,2-dichloroethane was substituted for 1,2-dibromoethane in the above run, and the reaction was otherwise carried out under the same reaction conditions, the yield of dimethyl cyclopropane-1,1-dicarboxylate was only 55% of theory.

EXAMPLE 1

Dimethyl cyclopropane-1,1-dicarboxylate by the method of this invention

A multi-neck glass flask equipped with a stirrer, a thermometer, a column section with phase separator for distillate, and a waste gas line was charged with 528 g of dimethyl malonate (4.0 mols), 1308 g of 1,2-dichloroethane (13.2 mols, 100 ml thereof in the phase separator), 1000 ml of dimethylformamide and 664 g (4.8 mols) of finely comminuted potassium carbonate. While stirring, the mixture was heated to 110° to 115° C.; a 1,2-dichloroethane/water azeotrope distilled over, which separated into an upper aqueous phase and a lower dichloroethane phase in the phase vessel. The dichloroethane phase was recycled into the reaction. Carbon dioxide escaped by way of the waste gas line. The temperature was raised to 120° C., and after 6 hours the reaction was complete. The salts were removed in two ways:

a) The volatile components were distilled out of the high boiling point components and out of the salts, at the end in vacuo, and the distillate was separated by distillation in a column.

b) The salts were filtered off, washed with dichloroethane or methanol, and dried.

After taking off the dichloroethane and dimethylformamide, which were reused for subsequent batches, the dimethyl cyclopropane-1,1-dicarboxylate distilled over at 85° C./18 mbar.

Yield: 525 g (83% of theory)
GC-purity: >99%

EXAMPLE 2

Diethyl cyclopropane-1,1-dicarboxylate by the method of the present invention

The apparatus described in Example 1 was successively charged with 320 g diethyl malonate (2.0 mols), 1000 ml dimethylformamide, 1308 g of 1,2-dichloroethane (13.2 mols) and 664 g (4.8 mols) of finely comminuted potassium carbonate. While thoroughly stirring, the mixture was heated to 115° C., whereupon release of carbon dioxide and separation of water commenced. Over a period of 3 hours, another 320 g of diethyl malonate (2.0 mols) were metered into the reaction vessel through a dropping funnel. After 6 hours, when no more water separated out, the reaction was complete.

Subsequently, the dichloroethane and, in vacuo, also the dimethylformamide, were distilled off. Diethyl cyclopropane-1,1-dicarboxylate was then distilled out of all salt and high boiling point residues in vacuo without using a column, and the distillate was subsequently rectified in a column.

Boiling point: 97° C./15 mbar
Yield: 630 g (83.8% of theory)
GC purity: 99%

EXAMPLE 3

1,1-Dicarbomethoxy-2-methylcyclopropane by the method of this invention

The apparatus described in Example 1 was charged successively with 132.1 g dimethyl malonate (1.0 mol), 166 g (1.2 mols) finely comminuted potassium carbonate, 339 g 1,2-dichloropropane (3.0 mols) and 250 ml of dimethylformamide. While stirring vigorously, the reaction mixture was heated to 118° C., and the reaction temperature was increased to 125° C. over a period of 15 hours. While releasing carbon dioxide, the reaction mixture distilled off as an azeotrope which was separated into dichloropropane and water in the phase separator and was then drained. Flash distillation was used to separate the salts and high boiling components, and the distillate was separated by way of a column into the fractions 1,2-dichloropropane, dimethylformamide and 1,1-dicarbomethoxy-2-methylcyclopropane. The target product distilled over at 78° C./14 mbar and was identified by means of H-NMR as the desired target product.

Yield: 79.8 g (45% of theory)
GC purity: 97.1%

EXAMPLE 4

1,1-Dicarboethoxy-2-methylcyclopropane

Using the same method as that described in Example 3, diethyl malonate was used to prepare 1,1-dicarboethoxy-2-methylcyclopropane. The product boiled at 101° C./14 mbar and was also identified by H-NMR.

Yield: 85.1 g (42% of theory)
GC purity: 98.8%

EXAMPLES 5 and 6

Transesterification of dimethyl cyclopropane-1,1-dicarboxylate into the corresponding diisopropyl ester or the corresponding di-n-butyl ester A 1-liter multi-neck flask equipped with a stirrer, thermometer and a 90 cm (including distillation sections) column was charged with 316.2 g of dimethyl cyclopropane-1,1-dicarboxylate (2.0 mols), 4 g of butyl titanate and 8.0 mols of isopropanol (481 g) or n-butanol (593 g). Under reflux, the mixture was heated to the boiling point until the temperature at the top of the column was the boiling point of methanol (65° C.); all of the methanol was distilled off with good reflux. In the case of diisopropyl cyclopropane-1,1-dicarboxylate the methanol distillation was complete after about 7 hours; in the case of di-n-butyl cyclopropane-1,1-dicarboxylate it was already complete after 3 hours. Thereafter, the excess alcohol was first distilled over in a water aspirator vacuum, and the target products were distilled over in an oil pump vacuum.

|  | Boiling Point (°C.) | Amount Obtained (g) | Yield (%) | GC Purity (%) |
| --- | --- | --- | --- | --- |
| diisopropyl ester | 103° C./15 mbar 63° C./0.8 mbar | 390.5 | 91.2 | 99.2 |
| di-n-butyl ester | 105° C./0.8 mbar | 451.5 | 93.2 | 98.9 |

The target compounds were identified by mass spectroscopy and both 1-H and 13-C-NMR spectra.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. The method of preparing a di-lower alkyl cyclopropane-1,1-dicarboxylate of the formula:

wherein

R is alkyl of 1 to 4 carbon atoms, and R' and R", which may be identical to or different from each other, are each hydrogen, methyl, ethyl or chlorine, provided that at least one of R' and R" is hydrogen, in the presence of dimethylformamide or dimethylacetamide, which comprises reacting a di-lower alkyl malonate of the formula

ROOC—CH$_2$—COOR  (II)

wherein

R has the same meanings as in formula I, with comminuted potassium carbonate having a particle size distribution of 85% or more smaller than 0.1 mm and 70% or more smaller than 0.05 mm, and with a 1,2-dichloroalkane of the formula

wherein

R' and R" have the same meanings as in formula I, at a temperature of 90° to 160° C.,
while continuously azeotropically distilling off the water released by the reaction, the molar ratio of dialkyl malonate: 1,2-dichloroalkane: potassium carbonate being 1: (2.5 to 3.5) : (1.0 to 1.4).

* * * * *